United States Patent
Subramanian et al.

(10) Patent No.: US 11,713,121 B2
(45) Date of Patent: Aug. 1, 2023

(54) AUTOMATED DETECTION AND REMEDIATION OF CONTAGION EVENTS

(71) Applicant: DISH Wireless L.L.C., Englewood, CO (US)

(72) Inventors: Prakash Subramanian, Littleton, CO (US); Nicholas B. Newell, Centennial, CO (US)

(73) Assignee: DISH Wireless L.L.C., Littleton, CO (US)

( * ) Notice: Subject to any disclaimer, the term of this patent is extended or adjusted under 35 U.S.C. 154(b) by 288 days.

(21) Appl. No.: 17/208,766

(22) Filed: Mar. 22, 2021

(65) Prior Publication Data

US 2022/0169382 A1 Jun. 2, 2022

Related U.S. Application Data

(60) Provisional application No. 63/120,360, filed on Dec. 2, 2020.

(51) Int. Cl.
*B64C 39/02* (2023.01)
*B64D 47/08* (2006.01)
(Continued)

(52) U.S. Cl.
CPC .............. *B64C 39/024* (2013.01); *A61L 2/24* (2013.01); *B64D 47/08* (2013.01);
(Continued)

(58) Field of Classification Search
CPC ...... B64C 39/024; A61L 2/24; A61L 2202/14; A61L 2202/16; B64D 47/08; B64U 10/13; B64U 2201/102; B64U 2101/30
See application file for complete search history.

(56) References Cited

U.S. PATENT DOCUMENTS 11,172,339 B1 * 11/2021 Hummer ................. H04W 4/38
2008/0056933 A1 * 3/2008 Moore ................. A47L 11/4011
422/4

(Continued)

FOREIGN PATENT DOCUMENTS

DE 102020105542 A1 9/2021

OTHER PUBLICATIONS

Kim, Max S., "South Korea is watching quarantined citizens with a smartphone app," MIT Technology Review, Sep. 19, 2022, 9 pages. https://www.technologyreview.com/2020/03/06/905459/ coronavirus-south-korea-smartphone-app-quarantine/.

(Continued)

*Primary Examiner* — Peter D Nolan
*Assistant Examiner* — Kenneth M Dunne
(74) *Attorney, Agent, or Firm* — Kilpatrick Townsend & Stockton LLP

(57) ABSTRACT

Techniques are provided for implementing automated contagion detection and remediation (ACDR) features to detect and remediate environmental contagion conditions. For example, ACDR techniques can be used to target contagion contamination on surfaces in a trafficked area, rather than focusing detecting and remediating human symptoms. ACDR systems can include swarms of specially configured drones under control of one or more centralized controllers to detect presence of one or more types of pathogens on surfaces and to classify detected contagion events. In some embodiments, upon such detection, the same or other specially configured drones can be triggered to remediate the detected condition by removing the pathogen by disinfecting surfaces, by cordoning off infected areas, and/or in other ways. Some embodiments can further log and aggregate data relating to detected contagion events to support tracking, (Continued)

remediation, enforcement, protocol updating, research, and/or other efforts.

20 Claims, 6 Drawing Sheets

(51) Int. Cl.
    *A61L 2/24*     (2006.01)
    *B64U 10/13*     (2023.01)
    *B64U 101/30*     (2023.01)

(52) U.S. Cl.
    CPC ....... *A61L 2202/14* (2013.01); *A61L 2202/16* (2013.01); *B64U 10/13* (2023.01); *B64U 2101/30* (2023.01); *B64U 2201/102* (2023.01)

(56) References Cited

U.S. PATENT DOCUMENTS

| | | |
|---|---|---|
| 2011/0093249 A1 | 4/2011 | Holmes et al. |
| 2011/0171065 A1* | 7/2011 | Park ..................... B05B 5/1608 239/548 |
| 2013/0318027 A1 | 11/2013 | Almogy et al. |
| 2015/0100330 A1 | 4/2015 | Shpits |
| 2016/0334276 A1* | 11/2016 | Pluvinage ............. B64C 39/024 |
| 2017/0024531 A1 | 1/2017 | Malaviya |
| 2018/0000575 A1* | 1/2018 | Fobi ..................... A01K 11/006 |
| 2020/0397936 A1* | 12/2020 | Deros ................. G05D 1/0221 |
| 2021/0290814 A1* | 9/2021 | Waterbury ................ A61L 2/10 |
| 2021/0363580 A1 | 11/2021 | Suliman et al. |
| 2021/0396905 A1* | 12/2021 | Neill ....................... G01V 3/32 |
| 2022/0142167 A1* | 5/2022 | Rader ....................... A61L 9/14 |
| 2022/0161251 A1* | 5/2022 | Spaventa ................ B01L 3/50 |

OTHER PUBLICATIONS

Leong et al., "Contact Tracing in Healthcare Digital Ecosystems for Infectious Disease Control and Quarantine Management," 2009 3$^{rd}$ IEEE International Conference on Digital Ecosystems and Technologies, 6 pages.

Riley et al., Transmission dynamics of the etiological agent of SARS in Hong Kong: impact of public health interventions. Science, 300(5627), 1961-1966. (Year: 2003).

Ferretti et al., "Quantifying dynamics of SARS-CoV-2 transmission suggests that epidemic control and avoidance is feasible though instantaneous digital contact tracing," MedRxiv. (Year: 2020).

* cited by examiner

AUTOMATED DETECTION AND REMEDIATION OF CONTAGION EVENTS

CROSS-REFERENCE TO RELATED APPLICATIONS

This application claims priority to U.S. Provisional Patent Application No. 63/120,360, filed on Dec. 2, 2020, entitled "Virus Detection Drones," the disclosure of which is hereby incorporated by reference in its entirety for all purposes.

FIELD

This invention relates generally to automated control systems, and, more particularly, to automated control of drones and/or other devices for detection and remediation of contagion events.

BACKGROUND

Conventionally, there is no practical way to keep track of where viruses and other contagions are present outside of monitoring and tracking people. A large amount of resources has been spent in recent times on testing humans to determine if they are infected, and on corresponding tracking, distancing, and remediation protocols. Particularly, in cases where no vaccine, and/or where personal protective equipment (PPE) is ineffective or impractical, there tends to be a reliance on social distancing and quarantines. However, social distancing tends only to be effective when distancing from another person or from a location known to be infected, and quarantining is retroactive. For example, a quarantined individual may have been infecting people and places for days prior to being tested and subsequently entering quarantine.

As an example, Donald goes hunting in the mountains. While there, he comes in contact with an infected animal. He returns to work on Monday without any symptoms. By Thursday, Donald begins to show symptoms, gets tested, and ends up in quarantine. In the first half of the work week, Donald was contagious, but asymptomatic. Meanwhile, he touched many surfaces subsequently touched by other individuals, and came into direct contact with many other individuals. Some or all of those other individuals may now be infected, and more will continue to become infected as the contagion spreads to an increasing number of people and remains on an increasing number of surfaces. As no one can see this happening, the contagion may have already spread rapidly to a large number of people and locations before any detection occurs and remedial action begins.

Thus, conventional approaches to limiting the spread of a contagion tend to be frustrated by the fact that the human eye cannot see contagions (even when a person is infected, the human eye can typically only see symptoms), and it may not be possible to know in many cases where and when to apply social distancing from other people, distancing from locations or objects, quarantines, etc. The result tends either to be an extreme over-application of protocols, causing detrimental economic and social impacts; or extreme under-application of protocols, allowing the contagion to continue to spread. As an example, by early 2021, despite significant global focus on various human protocols to limit its spread, the coronavirus (COVID-19) had claimed millions of lives worldwide and had an estimated impact on the global economy of trillions of dollars.

BRIEF SUMMARY

Among other things, embodiments provide automated contagion detection and remediation (ACDR) techniques to detect and remediate environmental contagion conditions. For example, ACDR techniques can be used to target contagion contamination on surfaces in a trafficked area, rather than focusing detecting and remediating human symptoms. ACDR systems can include swarms of specially configured drones under control of one or more centralized controllers to detect presence of one or more types of pathogens on surfaces and to classify detected contagion events. In some embodiments, upon such detection, the same or other specially configured drones can be triggered to remediate the detected condition by removing the pathogen by disinfecting surfaces, by cordoning off infected areas, and/or in other ways. Some embodiments can further log and aggregate data relating to detected contagion events to support tracking, remediation, enforcement, protocol updating, research, and/or other efforts.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

BRIEF DESCRIPTION OF THE DRAWINGS

The present disclosure is described in conjunction with the appended figures.

Figure 1:
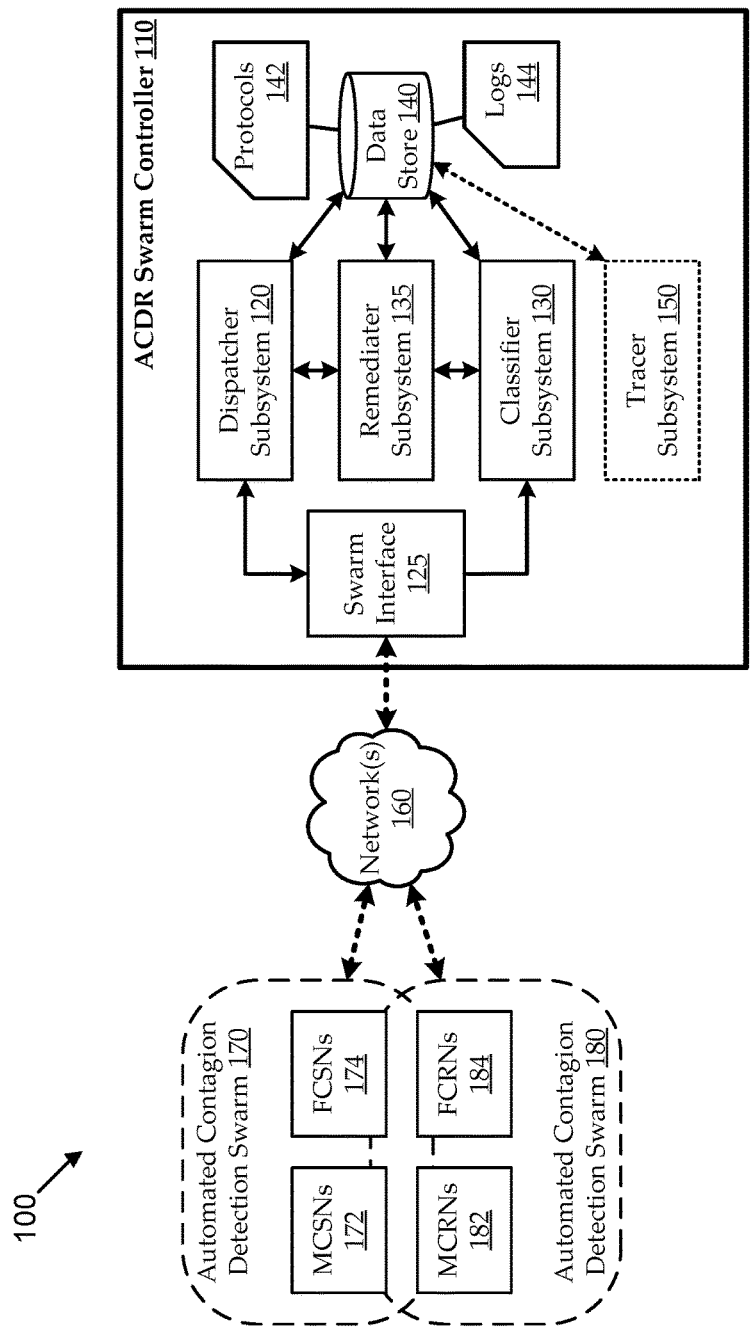
FIG. 1 shows an illustrative automated contagion detection and remediation (ACDR) system, according to embodiments described herein.

In the appended figures, similar components and/or features may have the same reference label. Further, various components of the same type may be distinguished by following the reference label by a second label (e.g., a lower-case letter) that distinguishes among the similar components. If only the first reference label is used in the specification, the description is applicable to any one of the similar components having the same first reference label irrespective of the second reference label.

DETAILED DESCRIPTION

Embodiments of the disclosed technology will become clearer when reviewed in connection with the description of the figures herein below. In the following description, numerous specific details are set forth to provide a thorough understanding of the present invention. However, one having ordinary skill in the art should recognize that the invention may be practiced without these specific details. In some instances, circuits, structures, and techniques have not been shown in detail to avoid obscuring the present invention.

Conventional approaches to limiting the spread of contagions (e.g., pathogens, viruses, etc.) tend to focus on testing humans to determine if they are infected, and on corresponding protocols for behavioral requirements (e.g., social distancing, wearing of personal protective equipment (PPE), etc.), tracking, and remediation. Ultimately, prevention often relies on the eventual discovery or invention, and sufficient distribution, of an effective vaccine. As the human eye cannot typically see such contagions, protocols tend to rely either on over-broad application of behavioral restrictions (e.g., quarantines, closing of businesses, etc.) and/or on detection and reporting of symptoms in carriers (e.g., infected humans) as indicators of a contagion location. As has been demonstrated during the COVID-19 pandemic, such conventional approaches tend to be ineffective at limiting the spread of contagions, and tend instead to wreak havoc on physical and mental health systems, on human development and socialization, and on economics.

Embodiments described herein implement automated contagion detection and remediation (ACDR) features to detect and remediate environmental contagion conditions. For example, ACDR techniques can be used to target contagion contamination on surfaces in a trafficked area, rather than focusing detecting and remediating human symptoms. ACDR systems can include swarms of specially configured drones under control of one or more centralized controllers to detect presence of one or more types of pathogens on surfaces and to classify detected contagion events. In some embodiments, upon such detection, the same or other specially configured drones can be triggered to remediate the detected condition by removing the pathogen by disinfecting surfaces, by cordoning off infected areas, and/or in other ways. Some embodiments can further log and aggregate data relating to detected contagion events to support tracking, remediation, enforcement, protocol updating, research, and/or other efforts.

FIG. 1 shows an illustrative automated contagion detection and remediation (ACDR) system 100, according to embodiments described herein. The ACDR system 100 includes a swarm controller 110, coupled via one or more networks 160 with an automated contagion detection swarm 170 and an automated contagion remediation swarm 180. In some embodiments, the ACDR system 100 is only the swarm controller 110, and the networks 160, automated contagion detection swarm 170, and automated contagion remediation swarm 180 are separate from, and in communication with the swarm controller 110. In other embodiments, the ACDR system 100 includes the swarm controller 110 and also some or all of the networks 160, automated contagion detection swarm 170, and/or automated contagion remediation swarm 180.

The swarm controller 110 generally controls operation of some or all of the automated contagion detection swarm 170 and the automated contagion remediation swarm 180. Embodiments of the automated contagion detection swarm 170 can include one or more mobile contagion sensor nodes (MCSNs) 172 and one or more fixed contagion sensor nodes (FCSNs) 174. Each node of the automated contagion detection swarm 170 includes one or more sensor or other component to detect conditions indicative of presence of a contagion. In one implementation, a node includes components to obtain air samples (e.g., fans, filters, etc.) for particulate measurement. In another implementation, a node includes contact components to obtain a physical surface sample (e.g., a surface swab) to obtain a measurements of particulates, etc. on the surface. In another implementation, a node includes non-contact components to obtain a physical surface sample (e.g., infrared, ultraviolet, and/or other optical detection components) to obtain measurements of particulates, etc. on the surface. In other implementations, one or more nodes include sensors for detecting surface and/or air temperature, humidity, optical spectra, and/or any other measurements that can be indicative of presence of one or more types of contagions. Some MCSNs 172 can further include components for proper handling of samples, such as for proper (e.g., sanitary, regulation compliant, etc.) disposal of samples, etc.

Embodiments of the automated contagion remediation swarm 180 can include one or more mobile contagion remediation nodes (MCRNs) 182 and one or more fixed contagion remediation nodes (FCRNs) 184. Each node of the automated contagion remediation swarm 180 includes one or more component to remediate conditions relating to presence of a contagion. Some implementations include components to disinfect an infected area, such as by deploying (e.g., spraying) disinfectant, physically wiping down surfaces, shining ultraviolet light at a surface, etc. Other implementations include components to cordon off an infected area. Some such implementations provide a physical cordoning, such as by assembling, activating, or holding up a physical barrier (e.g., a caution tape, a chain, a Plexiglas barrier, etc.). Other such implementations provide an optical barrier, such as by projecting a warning sign on a floor or a surface to indicate an infected area, and/or by flashing warning lights, etc. Other such implementations provide an audible barrier, such as by sounding an alarm, playing a recorded warning message, etc.

The MCSNs 172 and the MCRNs 182 include at least one drone, which can generally include any fully autonomous, or partially autonomous, vehicle under at least partial control of the swarm controller 110 to perform contagion detection and/or remediation tasks. Such vehicular drones can be in communication with the swarm controller 110, can receive commands from the swarm controller 110, and can report back detection events (e.g., measurements) to the swarm controller 110. Embodiments of such mobile nodes can include any suitable components for implementing mobile functions. For example, embodiments can include transport components (e.g., wheels, rotors, etc.), landing and/or stabilizing components (e.g., skid pads, stabilizing arms, etc.), protective components (e.g., bumpers, roll bars, etc.), etc. In some implementations, one or more of the mobile nodes includes physical access components for physically accessing particular locations. For example, a drone can include armatures configured to open a door handle, push open a door, etc.; probes configured to open a lock, push an elevator button, enter a code into a keypad, etc.); wireless access components to interface with electronic locks, radiofrequency identification (RFID) readers, etc.; and/or any other suitable components.

As illustrated, the automated contagion detection swarm 170 and the automated contagion remediation swarm 180 can at least partially overlap. For example, in some implementations, a same drone can include both components for implementing a MCSN 172 and components for implementing a MCRN 182. In such an implementation, the drone is directed by the swarm controller 110 to use whichever of its components supports performance of particular detection and/or remediation tasks, as appropriate. In context of the automated contagion detection swarm 170, the drone can be a quadcopter, or any other suitable flying, driving, or otherwise mobile carrier for one or more MCSNs 172. For example, a flying drone includes electromechanical components to land on, and/or hover next to, a surface, swab the surface to obtain a sample, obtain a measurement from the sample, and report back the measurement to the swarm controller 110 (e.g., each time, periodically, only when the measurement indicates a contagion event, etc.). In context of the automated contagion remediation swarm 180, the drone can be a quadcopter, or any other suitable flying, driving, or otherwise mobile carrier for one or more MCRNs 182. For example, a flying drone includes electromechanical components to land on, and/or hover next to, a surface, spray the surface with disinfectant, and report back to the swarm controller 110 (e.g., each time, periodically, only after completion of a remediation protocol, as described below, etc.).

The FCSNs 174 and FCRNs 184 can include the same or other types of sensor components as the MCSNs 172 and MCRNs 182, respectively, but implemented in a substantially fixed platform. Though these nodes are referred to as "fixed," they may have moving components, such as for pointing, redirecting, etc. For example, such nodes can be implemented in a wall-mounted housing that can have certain portions configured to be manually positioned (e.g., upon installation by a human installer) and/or electromechanically positioned (e.g., dynamically by the swarm controller 110). As noted above, the automated contagion detection swarm 170 and the automated contagion remediation swarm 180 can at least partially overlap. For example, in some implementations, a same substantially fixed housing and/or mounting hardware can be used to support both components for implementing a FCSN 174 and components for implementing a FCRN 184. In context of the automated contagion detection swarm 170, the FCSNs 174 can include air quality (e.g., temperature, humidity, particulate, etc.) sensors, video cameras, microphones, and/or any other suitable sensors for contagion detection. The particular sensors can be integrated in a housing, and the housing may or may not permit focusing, pointing, and/or other types of movement of the sensor with respect to the wall mounting hardware. For example, an FCSN 174 can include a video camera mounted in a corner of a room to record video of the room environment; the swarm controller 110 can control the video camera to pan and/or tils the camera, zoom in or out, focus, change spectrum (e.g., record visible-spectrum video or infrared video), etc. In the context of the automated contagion remediation swarm 180, the FCRNs 184 can include the same or other types of remediation components as the MCRNs 182, but implemented in a substantially fixed platform. For example, a FCRN 184 can include a disinfectant sprayer, ultraviolet lamp (e.g., ultraviolet germicidal radiation (UVGI) system), or the like, that is mounted in a fixed location near the ceiling at a corner of a room and configured to be rotated electromechanically (e.g., under control of the swarm controller 110) to point its remediation components into different areas of the room from its fixed location in the corner.

Embodiments of the swarm controller 110 include the swarm interface 125 to facilitate communications between the swarm controller 110 and the automated contagion detection swarm 170 and the automated contagion remediation swarm 180 via any suitable one or more communication networks 160. Merely by way of example, the networks 160 can include a satellite cable network, a wireline network, an optical fiber network, a telecommunications network, an intranet, an Internet, a local area network (LAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In some embodiments, the networks 160 include one or more network access points, such as wired or wireless network access points (e.g., base stations and/or internet exchange points). In some embodiments, the FCSNs 174 and/or FCRNs 184 are in communication with the swarm interface 125 via any suitable wired or wireless network, or combination thereof. In some such embodiments, one or more FCSNs 174 and/or FCRNs 184 are coupled with the swarm interface 125 using Ethernet cables, optical fiber cables, coaxial cables, and/or any other suitable cables. In other such embodiments, one or more FCSNs 174 and/or FCRNs 184 are implemented as Internet of Things (IoT) devices and are coupled with the swarm interface 125 over an IoT network. In other embodiments, one or more FCSNs 174 and/or FCRNs 184 include wireless communication ports, and/or the like, to communicate with the swarm controller 110 via a WLAN, such as using wireless fidelity (WiFi), or the like. Embodiments of the mobile nodes of the swarms (i.e., the MCSNs 172 and/or MCRNs 182) are typically in communication with the swarm interface 125 via at least one suitable wireless network link. For example, some or all of the MCSNs 172 and/or MCRNs 182 are configured as IoT devices, WiFi devices, etc. Some embodiments are configured for so-called "hub and spoke" communications, such that the swarm interface 125 is essentially a hub, and the various automated contagion detection swarm 170 and automated contagion remediation swarm 180 nodes are spokes. In other embodiments, some or all of the automated contagion detection swarm 170 and automated contagion remediation swarm 180 nodes are configured to establish a mesh network, such as one or more ad hoc networks.

Different embodiments can implement the automated contagion detection swarm 170 and/or the automated contagion remediation swarm 180 with different levels of autonomy. In some implementations, some or all nodes of the automated contagion detection swarm 170 and the automated contagion remediation swarm 180 are under full control of the swarm controller 110. For example, they are "autonomous" in the sense that the swarm controller 110 automatically controls them (i.e., without relying on human input), even though the nodes themselves are under full control of another system. In other implementations, some or all nodes of the automated contagion detection swarm 170 and the automated contagion remediation swarm 180 are configured to autonomously perform preset routines (e.g., functions, protocols, etc.), and the swarm controller 110 instructs performance of those routines. For example, the swarm controller 110 may instruct a MCSN 172 to patrol an area for contagion detection, and the MCSN 172 may autonomously execute that patrol, including autonomously controlling its own position (e.g., self-driving, avoiding obstacles, etc.), autonomously determining when and where to obtain samples and/or other measurements, autonomously determining when to return to a base for charging, autonomously determining when to report measurements back to the swarm controller 110, etc. Some embodiments of the automated contagion detection swarm 170 and/or the automated contagion remediation swarm 180 are configured to operate as a swarm, rather than as individual nodes. For example, the swarm controller 110 can direct the automated contagion remediation swarm 180 to cover a particular infected area with disinfectant, and the nodes of the automated contagion remediation swarm 180 can communicate with each other to dynamically plan and execute an optimized routine among the various nodes.

Embodiments of the swarm controller 110 include some or all of a dispatcher subsystem 120, a swarm interface 125, a classifier subsystem 130, a remediater subsystem 135, and a data storage subsystem 140. Embodiments of the data storage subsystem 140 can include any suitable types of data storage for storing the various types of data, as described herein, such as remote storage (e.g., a remote server), distributed storage (e.g., cloud-based storage), local storage (e.g., one or more solid-state drives, hard disk drives, tape storage systems, etc.), and/or other storage. In some implementations, the data storage subsystem 140 is implemented as a component of the swarm controller 110. For example, the data storage subsystem 140 is collocated in a single computational environment with other components of the swarm controller 110. In other embodiments, the data storage subsystem 140 is remote from, but accessible to, other components of the swarm controller 110 (e.g., implemented in a cloud computing framework).

The data storage subsystem 140 can store one or more contagion protocols 142 that define information relating to one or more contagions. The contagion protocols 142 can include definition information, such as contagion name, severity, seasonality, reproduction number, etc. The contagion protocols 142 can also define detection patrol protocols, such as the types of regions that can carry the contagion (e.g., does the contagion tend to stay on surfaces and/or for how long, does the contagion travel by air and/or how far, etc.), how often to revisit a same location to detect whether the contagion is present there, what types of detection means are effective for the particular contagion, etc. In some implementations, the detection patrol protocols are defined in a results-based manner, such as by indicating a patrol region (e.g., a defined area, a set of locations, etc.) over which the automated contagion detection swarm 170 is to obtain physical measurement data to at least a predefined spatial resolution (e.g., the measurement locations are separated by a threshold maximum, average, or other distance measurement) and measurement frequency (e.g., each measurement a location is obtained within a threshold amount of time since the last measurement obtained in that same, or comparable, location). The contagion protocols 142 can also define trigger condition protocols for the contagions, such as what types of measurements and what corresponding levels of those measurements tend to indicate presence of such a contagion. The contagion protocols 142 can also define remediation protocols for the contagions, such as whether isolation from a location is effective (e.g., and what types of isolation, for how long, etc.), whether disinfectant of a location is effective (e.g., and what types of disinfectants, quantities, applications, etc.), etc. As described herein, embodiments of the data storage subsystem 140 can also store other types of information, such as logs 144.

Embodiments of the dispatcher subsystem 120 wirelessly schedule and direct the automated contagion detection swarm 170 to execute a contagion detection patrol of a physical region. The patrolled regions can be any suitably trafficked region, such as a shopping mall, grocery store, entertainment park, business office, home, hotel, conference center, etc. The patrol can be scheduled and directed in accordance with a detection patrol protocol stored by the data storage subsystem 140. The patrols can be fully controlled by the dispatcher subsystem 120 (e.g., the dispatcher subsystem 120 can effectively drive MCSNs 172 around patrol routes), the patrols can be fully automated (e.g., the MCSNs 172 can be directed to patrol, and the MCSNs 172 can autonomously determine the manner in which to execute the command), etc. In some implementations, the dispatcher subsystem 120 executes the patrol as a single (e.g., on-demand) patrol. For example, the dispatcher subsystem 120 is configured to execute patrols according to a predetermined schedule, or in response to receiving a directive (e.g., from a human operator, from another component of the swarm controller 110, etc.). In some embodiments, the dispatcher subsystem 120 is configured to continuously run patrols. For example, portions of the automated contagion detection swarm 170 can be continuously on patrol (e.g., around the clock, only during certain timeframes, etc.), except when a particular node is charging, incapacitated, in need of replenishment or repair (e.g., where detection and/or other components are expended over time), etc.

During the patrol, one or more MCSNs 172 obtain samples and/or measurements relating to contagion detection. In some cases, one or more FCSNs 174 also obtain samples and/or measurements relating to contagion detection. As noted above, the locations, timing, and/or types of samples and/or measurements can be obtained based on the contagion protocols 142. Some or all of the obtained samples and/or measurements can be considered as a potential trigger condition that corresponds to a type, level, combination, etc. of measurements indicative of presence of a contagion (e.g., according to the contagion protocols 142). Some trigger conditions can relate to direct detection of contagion, such as a MCSN 172 detecting presence of a particular bacterium or virus on a surface, or a MCSN 172 or FCSN 174 detecting such a presence in the air. For example, an implementation of a MCSNs 172 can be configured as a non-contact mobile imaging platform for digital bioassays. Other trigger conditions can relate to indirect detection of contagion indicators, such as by a FCSN 174 detecting a human with excessive body temperature, detecting a characteristic sound of a type of cough, detecting a characteristic type of person-to-person interaction (e.g., two individuals standing within a particular proximity of each other for a particular amount of time, an individual walking through a populated area without a mask, etc.), detecting a characteristics type of person-to-surface interaction (e.g., an individual touching a surface without protection), etc. As described herein, some embodiments of the swarm controller 110 are focused on detection of environmental contagion conditions (e.g., on surfaces, in the air, etc.), and not on human symptomatic detection and remediation. For some of those embodiments, however, types of indirect detection described above can be used to supplement direct detection. For example, direct detection may indicate possible presence of a bacteria that sometimes indicates a particular type of contagion, and other indirect detection information (e.g., detection of an excessive amount of coughing or sneezing, elevated human temperatures, etc.) can provide further circumstantial support for the presence of the contagion. Some embodiments can permit further circumstantial detection information, such as notifications from human users, separate systems, and/or other origins. For example, a human or machine can submit a notification of a potential contagion event via an application or computational portal (e.g., a smartphone app or website), via a telephone call, via an application programming interface (API) from an interfacing computational system, etc.

Embodiments of the classifier subsystem 130 analyze the detected set of candidate trigger conditions obtained by one or more of the MCSNs 172 (e.g., and FCSNs 174 in some cases) during execution of the contagion detection patrol to classify an associated contagion trigger event into one of multiple event classes. The event classes can include a "definite contagion event," a "definite no-contagion event," and a "likely contagion event." In some implementations, the event classes include one or more additional classes, such as an "unlikely contagion event." Each class can be identified as part of the contagion protocols 142. For example, the contagion protocols 142 can define a definite contagion event as anytime the detected set of candidate trigger conditions includes at least one of a predefined set of measurement types and/or measurement levels. In some embodiments, the classifying involves comparing the detected set of candidate trigger conditions to the contagion protocols 142. In some embodiments, some or all of the measurement data obtained by the automated contagion detection swarm 170 is received as raw data at the classifier subsystem 130, and the analyzing by the classifier subsystem 130 includes converting the raw data into data that can be classified according to the contagion protocols 142. For example, the classifier subsystem 130 is configured to convert, parse, filter, and/or otherwise process the data. In other embodiments, the automated contagion detection swarm 170 is configured to obtain and/or communicate some or all of its obtained detection information in a form that is directly usable by the classifier subsystem 130. For example, a particular MCSN 172 can swab a surface and perform an onboard analysis of the swabbed surface sample to obtain a measurement, and the classifier subsystem 130 can receive and analyze the measurement directly in context of the contagion protocols 142. In some embodiments, the analysis by the classifier subsystem 130 includes combining data from multiple nodes of the automated contagion detection swarm 170 and/or over time. For example, the classifier subsystem 130 can generate computed data from the obtained data by computing statistics and/or trends from the data, interpolating and/or extrapolating the data, weighting and combining the data, computing an average of the data, aggregating the data at one or more levels, etc.; and the analyzing can be performed at least partially on the computed data.

Figure 2:
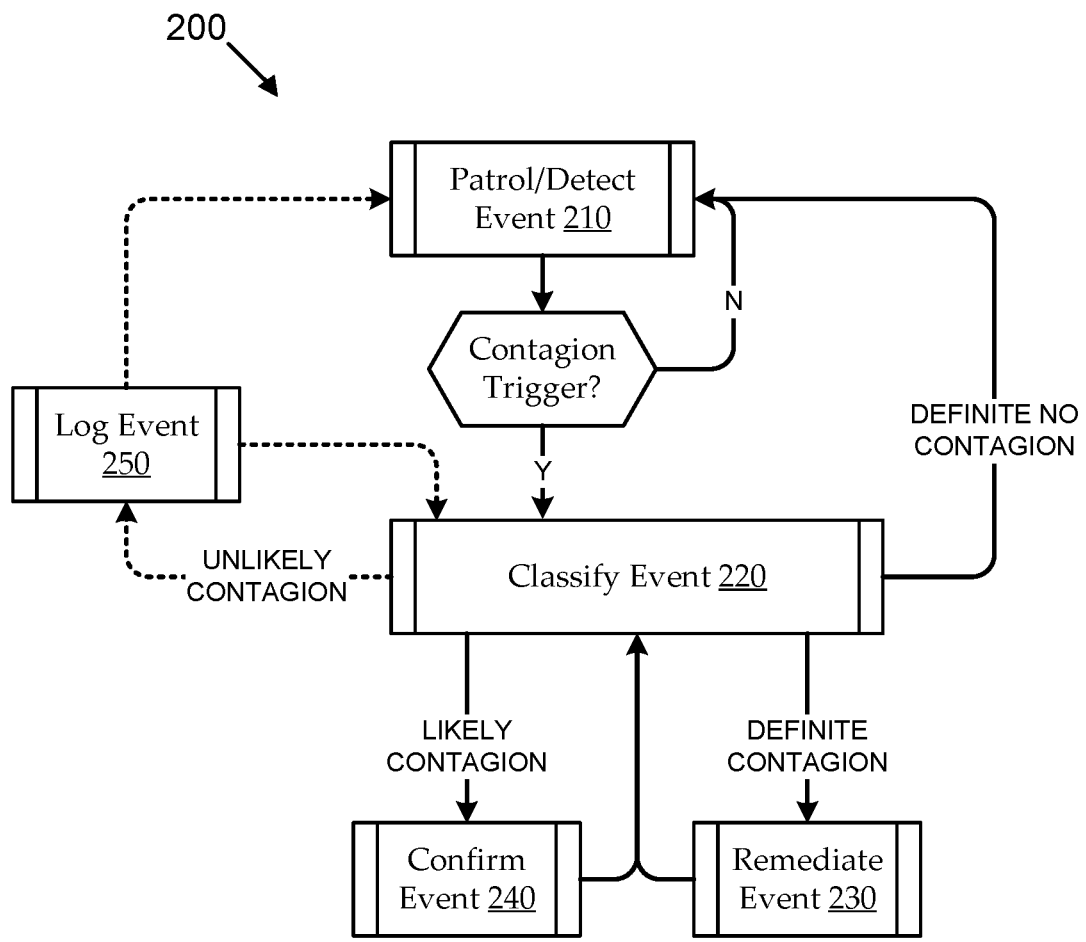
FIG. 2 shows a simplified flow diagram of operation of the swarm controller, according to various embodiments.

Embodiments of the remediater subsystem 135 are coupled with the dispatcher subsystem 120 and the classifier subsystem 130 to respond to the contagion trigger event in accordance with the event class determined by the classifier subsystem 130. For added clarity, FIG. 2 shows a simplified flow diagram 200 of operation of the swarm controller 110, according to various embodiments. As shown, embodiments can iteratively patrol for detection of a contagion event 210 until a contagion trigger is detected. When information from the patrol indicated that a potential contagion event has been detected, the event can be classified 220 by the classifier subsystem 130. As noted above, the classification 220 can result in the event being identified as a definite no-contagion event, as a definite contagion event, or as a likely contagion event. In some implementation, the classification 220 can further result in the event being considered as an unlikely contagion event.

In response to the classifier subsystem 130 classifying the contagion trigger event as a definite no-contagion event, some embodiments of the remediater subsystem 135 essentially do nothing. For example, having determined conclusively that there is no contagion event of concern, the remediater subsystem 135 can continue to wait until some remediation action is called for. This is indicated in FIG. 2 by an arrow labeled with "definite no-contagion event" returning from the classifying 220 to the patrolling/detecting 210 without further action. In some embodiments, even when the classifier subsystem 130 classifies the contagion trigger event as a definite no-contagion event, the remediater subsystem 135 can log the event in the stored logs 144.

In response to the classifier subsystem 130 classifying the contagion trigger event as a definite contagion event, the remediater subsystem 135 can remediate the event 230, as illustrated in FIG. 2. The remediating 230 can include assigning a set of contagion remediation actions to at least a portion of the automated contagion remediation swarm 180 based on the contagion protocols 142. The remediater subsystem 135 can also direct the dispatcher subsystem 120 to dispatch the portion of the automated contagion remediation swarm 180 to remediate the definite contagion event based on the set of contagion remediation actions. In some embodiments, the remediation includes assigning at least one drone, as one or more of the MCRNs 182 of the automated contagion remediation swarm 180, to execute a disinfecting routine in an infected physical area associated with the trigger event. For example, such a disinfecting routine can involve using the one or more MCRNs 182 (e.g., and FCSNs 174 in some cases) to apply disinfectant to one or more surfaces and/or in the air, to wipe down surfaces, to shine ultraviolet light into an area, etc. In other embodiments, the remediation includes assigning at least one drone, as one or more of the MCRNs 182 of the automated contagion remediation swarm 180, to execute a cordoning routine around an infected physical area associated with the trigger event. For example, the cordoning routine can include erecting or positioning a physical barrier (e.g., caution tape) around at least a portion of the area, projecting an optical warning signal in and/or near the infected area, sounding an audible alarm or prerecorded message, and/or otherwise conspicuously indicating that an area is infected.

In some embodiments, the remediater subsystem 135 performs additional tasks in response to the classifier subsystem 130 classifying the contagion trigger event as a definite contagion event. In some such embodiments, the remediater subsystem 135 can use various techniques to determine an infected area, which is then used to define an area for remediation. For example, the remediater subsystem 135 can direct the dispatcher subsystem 120 to dispatch a portion of the automated contagion detection swarm 170 to a location associated with the detected set of candidate trigger conditions to obtain a set of surrounding physical measurement points, and the remediater subsystem 135 can define the infected physical area for remediation based on the physical measurement points. In some embodiments, subsequent to dispatching the portion of the automated contagion remediation swarm 180 to remediate the infected area, the remediater subsystem 135 can receive information from the portion of the automated contagion remediation swarm 180 indicating that the definite contagion event is remediated. In respond to that information, the remediater subsystem 135 can direct the classifier subsystem 130 to reclassify the definite contagion event as a definite no-contagion event. For example, as illustrated in FIG. 2, after remediating the event 230, embodiments can return to the classifying 220 to make sure the remediated area is now being classified as a definite no-contagion event (thereby returning to the patrolling/detecting 210). In some embodiments, subsequent to taking remediation actions, the swarm controller 110 can force a patrol of the remediated area to obtain new measurements and to confirm that the new measurements result in a definite no-contagion event classification. For example, after remediating the event 230 in FIG. 2, embodiments can return to the patrolling/detecting 210, or can otherwise force collection of additional information. After remediation activities are concluded in an area, some embodiments of the remediater subsystem 135 can perform clean-up tasks, such as to notify individuals and/or entities that the area is remediated, and/or to stop cordoning off areas (e.g., by removing alarms and barriers).

In response to the classifier subsystem 130 classifying the contagion trigger event as a likely contagion event, the remediater subsystem 135 can assign a set of contagion detection actions to at least a portion of the automated contagion detection swarm 170 based on comparing the detected set of candidate trigger conditions to the stored contagion protocols 142. For example, classification as a likely contagion event can indicate that some of the information obtained from the detection patrol indicates a possible contagion event, but the information is not sufficiently conclusive. As such, the remediater subsystem 135 can use the contagion protocols 142 to determine which information, in addition to the obtained information from the patrol, would tend to lead to a more conclusive result. To obtain the additional information, embodiments of the remediater subsystem 135 can direct the dispatcher subsystem 120 to dispatch the portion of the automated contagion detection swarm 170 to obtain a further set of candidate trigger conditions based on the comparing. As the further information is obtained (e.g., or after all the additional information is obtained), the remediater subsystem 135 can direct the classifier subsystem 130 to reclassify the trigger condition based on the further set of candidate trigger conditions. As illustrated in FIG. 2, embodiments can use such techniques to confirm the event 240 either as a definite contagion event or a definite no-contagion event, which can involve and/or result in returning to the classifying 220. In some embodiments, the event is iteratively re-classified until a definitive classification (i.e., as one of definite contagion event or a definite no-contagion event) can be obtained.

As noted above, some embodiments further support an "unlikely contagion event" classification. In response to the classifier subsystem 130 classifying the contagion trigger event as an unlikely contagion event, the remediater subsystem 135 can log the unlikely contagion event (illustrated as logging the event 250 in FIG. 2) in an event log 144 and determine whether a previous contagion trigger event was previously logged in the event log 144 that corresponds to the present contagion trigger event. For example, characteristics (e.g., measurements, location, timing, etc.) of the present trigger event can be compared against those of previously logged contagion trigger events to determine an amount of correlation between the events. If the correlation is sufficiently high, the correlation can indicate that the otherwise unlikely contagion event should be considered as a likely contagion event. In such a case, embodiments of the remediater subsystem 135 can direct the classifier subsystem 130 to reclassify the present contagion trigger event as a likely contagion event and can perform remediation tasks in a manner consistent with the event being classified by the classifier subsystem 130 as a likely contagion event (e.g., indicated by the arrow from logging the event 250 in FIG. 2 returning to the classifying 220). If there is no, or insufficient, correlation between the present event and previously logged events, embodiments can simply continue to further patrolling and detection (e.g., as indicated in FIG. 2 by the arrow back to the patrolling and detecting 210).

Returning to FIG. 1, embodiments of the swarm controller 110 can update the logs 144 to indicate any suitable information about the contagion event. For example, the logs 144 can be updated to record what type of event was classified (e.g., when and where the event occurred, the type of contagion detected, the types of data used to classify the event, the density of that information, which nodes obtained that information, etc.), what remediation actions were taken (e.g., and/or whether the remediation was subsequently verified), etc. The logs 144 can be used for any suitable purpose, such as to provide circumstantial support for a further classification (e.g., as in classifying unlikely contagion events), for tracking the spread of a contagion, for aggregating with information collected by other systems in other locations, etc.

Some embodiments of the swarm controller 110 also include a tracer subsystem 150. In some embodiments, the tracer subsystem 150 is a component of the swarm controller 110. In other embodiments, the swarm controller 110 includes APIs, or other components, for communicating with a separate tracer subsystem 150. In some embodiments, the tracer subsystem 150 gathers information from the logs 144, such as round trip intervals of the automated contagion detection swarm 170 and/or the automated contagion remediation swarm 180 nodes, infection intervals of various contagions, infection area maps indicating locations of contagion events, etc. Some embodiments of the tracer subsystem 150 use various techniques to trace a contagion event to a particular individual and/or to a particular occurrence (e.g., a meeting in a conference room). A time interval can be determined in association with a particular contagion event, which can be considered as a an infection interval. For example, the infection interval can be based on the round-trip times of portions of the automated contagion detection swarm 170, on detection patrol protocols, on how long a particular contagion is known to remain on a particular type of surface, etc. Video analysis, or the like, can be used to determine people and/or objects that came in contact with an infected area. Sample characteristics (e.g., location, timing, density, measurement level, etc.), event characteristics (e.g., interpersonal contact events detected during video analysis), surface characteristics (e.g., known contagion-related properties of different types of materials), and/or other information can be used to approximate the timing of an originating infection event (e.g., when an infected individual likely touched a particular surface, etc.) and to narrow down likely infected subjects. If there are multiple potential human subjects, techniques can be used to further narrow down the list of possible subjects of concern. For example, further video or other analysis can help determine which individual or individuals were closest to the densest contagion distribution at the time of interest, if a same person was identified in any other infection intervals from other portions of the automated contagion detection swarm 170 at other locations, etc. These and/or other techniques can be applied recursively to reach a likely source (or individual sources) of infection. Once identified, informative and/or remedial action can be taken. For example, a communication can be sent to identified individuals (e.g., by text, email, SMS, etc.), diagnostic tests can be scheduled for those individuals (e.g., by requiring a self-test, by making a doctor's appointment, by delivering a test kit, etc.), etc. In some such cases, techniques can be used to ensure compliance with privacy policies and/or regulatory regimes (e.g., the European Union's General Data Protection Regulation 2016/679 (GDPR), the United States' Health Insurance Portability and Accountability Act of 1996 (HIPAA), etc.). Some embodiments can use the information to inform further actions of the swarm controller 110. For example, embodiments can automatically schedule a surveillance drone of the automated contagion detection swarm 170 for some period of time (e.g., the next 14 days) to monitor individuals and/or locations of concern to help identify further contagion contact and potential spread.

Some embodiments can also provide access (e.g., anonymized or not) to collected data, video footage of contagion events, and/or the like for any suitable purpose, such as to help correct bad habits, for regulatory compliance, for public notification and/or education, etc. Some embodiments can interface with systems configured for network tracking of contagion propagation through host populations, such as those described in U.S. patent application Ser. No. 16/839,697, filed on Apr. 3, 2020, titled "Network Tracking of Contagion Propagation Through Host Populations," which is hereby incorporated by reference in its entirety.

Figure 3:
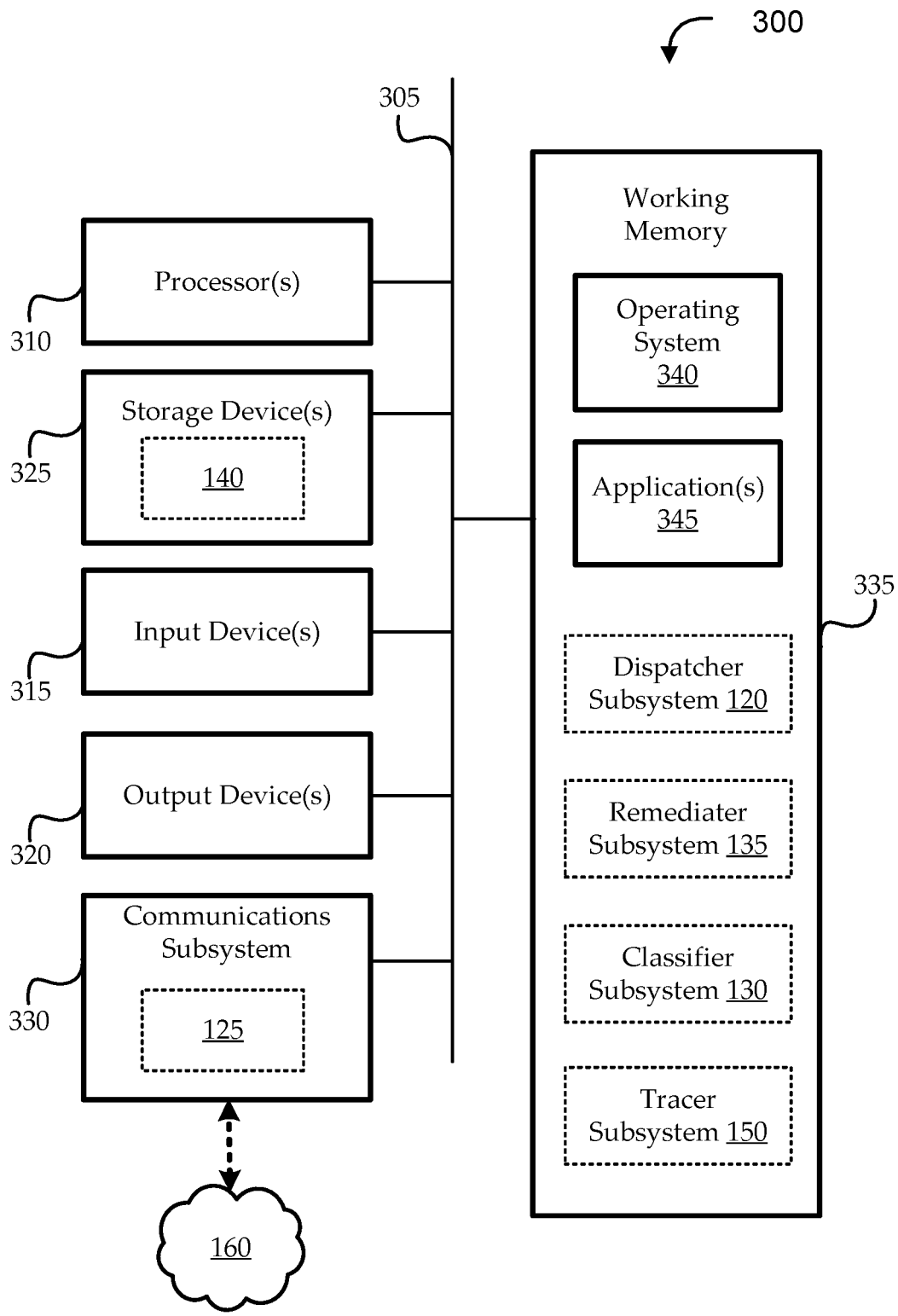
FIG. 3 provides a schematic illustration of one embodiment of a computer system that can implement various system components and/or perform various steps of methods provided by various embodiments.

Embodiments of the swarm controller 110, or components thereof, can be implemented on, and/or can incorporate, one or more computer systems, as illustrated in FIG. 3. FIG. 3 provides a schematic illustration of one embodiment of a computer system 300 that can implement various system components and/or perform various steps of methods provided by various embodiments. It should be noted that FIG. 3 is meant only to provide a generalized illustration of various components, any or all of which may be utilized as appropriate. FIG. 3, therefore, broadly illustrates how individual system elements may be implemented in a relatively separated or relatively more integrated manner.

The computer system 300 is shown including hardware elements that can be electrically coupled via a bus 305 (or may otherwise be in communication, as appropriate). The hardware elements may include one or more processors 310, including, without limitation, one or more general-purpose processors and/or one or more special-purpose processors (such as digital signal processing chips, graphics acceleration processors, video decoders, and/or the like); one or more input devices 315; and one or more output devices 320. In some implementations, the computer system 300 is a server computer configured to interface with additional computers, such that the input devices 315 and/or output devices 320 include various physical and/or logical interfaces (e.g., ports, etc.) to facilitate computer-to-computer interaction and control.

The computer system 300 may further include (and/or be in communication with) one or more non-transitory storage devices 325, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable and/or the like. Such storage devices may be configured to implement any appropriate data stores, including, without limitation, various file systems, database structures, and/or the like. In some embodiments, the storage devices 325 include the data storage subsystem 140. For example, the storage devices 325 can store the contagion protocols 142, the logs 144, and/or other relevant information.

The computer system 300 can also include a communications subsystem 330, which can include, without limitation, a modem, a network card (wireless or wired), an infrared communication device, a wireless communication device, and/or a chipset (such as a Bluetooth™ device, an 302.11 device, a WiFi device, a WiMax device, cellular communication device, etc.), and/or the like. As described herein, the communications subsystem 330 supports multiple communication technologies. Further, as described herein, the communications subsystem 330 can provide communications with one or more communication networks 160. Embodiments of the communications subsystem 330 can also implement components of features of the swarm interface 125 to facilitate communication with the automated contagion detection swarm 170 and the automated contagion remediation swarm 180 via the network(s) 160.

In many embodiments, the computer system 300 will further include a working memory 335, which can include a RAM or ROM device, as described herein. The computer system 300 also can include software elements, shown as currently being located within the working memory 335, including an operating system 340, device drivers, executable libraries, and/or other code, such as one or more application programs 345, which may include computer programs provided by various embodiments, and/or may be designed to implement methods, and/or configure systems, provided by other embodiments, as described herein. Merely by way of example, one or more procedures described with respect to the method(s) discussed herein can be implemented as code and/or instructions executable by a computer (and/or a processor within a computer); in an aspect, then, such code and/or instructions can be used to configure and/or adapt a general purpose computer (or other device) to perform one or more operations in accordance with the described methods. In some embodiments, the operating system 340 and the working memory 335 are used in conjunction with the one or more processors 310 to implement features of the swarm controller 110. For example, the operating system 340 and the working memory 335 are used in conjunction with the one or more processors 310 to implement some or all of the dispatcher subsystem 120, the remediater subsystem 135, the classifier subsystem 130, and the tracer subsystem 150.

A set of these instructions and/or codes can be stored on a non-transitory computer-readable storage medium, such as the non-transitory storage device(s) 325 described above. In some cases, the storage medium can be incorporated within a computer system, such as computer system 300. In other embodiments, the storage medium can be separate from a computer system (e.g., a removable medium, such as a compact disc), and/or provided in an installation package, such that the storage medium can be used to program, configure, and/or adapt a general purpose computer with the instructions/code stored thereon. These instructions can take the form of executable code, which is executable by the computer system 300 and/or can take the form of source and/or installable code, which, upon compilation and/or installation on the computer system 300 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware can also be used, and/or particular elements can be implemented in hardware, software (including portable software, such as applets, etc.), or both. Further, connection to other computing devices, such as network input/output devices, may be employed.

As mentioned above, in one aspect, some embodiments may employ a computer system (such as the computer system 300) to perform methods in accordance with various embodiments of the invention. According to a set of embodiments, some or all of the procedures of such methods are performed by the computer system 300 in response to processor 310 executing one or more sequences of one or more instructions (which can be incorporated into the operating system 340 and/or other code, such as an application program 345) contained in the working memory 335. Such instructions may be read into the working memory 335 from another computer-readable medium, such as one or more of the non-transitory storage device(s) 325. Merely by way of example, execution of the sequences of instructions contained in the working memory 335 can cause the processor(s) 310 to perform one or more procedures of the methods described herein.

The terms "machine-readable medium," "computer-readable storage medium" and "computer-readable medium," as used herein, refer to any medium that participates in providing data that causes a machine to operate in a specific fashion. These mediums may be non-transitory. In an embodiment implemented using the computer system 300, various computer-readable media can be involved in providing instructions/code to processor(s) 310 for execution and/or can be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the non-transitory storage device(s) 325. Volatile media include, without limitation, dynamic memory, such as the working memory 335. Common forms of physical and/or tangible computer-readable media include, for example, a floppy disk, a flexible disk, hard disk, magnetic tape, or any other magnetic medium, a CD-ROM, any other optical medium, any other physical medium with patterns of marks, a RAM, a PROM, EPROM, a FLASH-EPROM, any other memory chip or cartridge, or any other medium from which a computer can read instructions and/or code. Various forms of computer-readable media may be involved in carrying one or more sequences of one or more instructions to the processor(s) 310 for execution. Merely by way of example, the instructions may initially be carried on a magnetic disk and/or optical disc of a remote computer. A remote computer can load the instructions into its dynamic memory and send the instructions as signals over a transmission medium to be received and/or executed by the computer system 300.

The communications subsystem 330 (and/or components thereof) generally will receive signals, and the bus 305 then can carry the signals (and/or the data, instructions, etc., carried by the signals) to the working memory 335, from which the processor(s) 310 retrieves and executes the instructions. The instructions received by the working memory 335 may optionally be stored on a non-transitory storage device 325 either before or after execution by the processor(s) 310.

It should further be understood that the components of computer system 300 can be distributed across a network. For example, some processing may be performed in one location using a first processor while other processing may be performed by another processor remote from the first processor. Other components of computer system 300 may be similarly distributed. As such, computer system 300 may be interpreted as a distributed computing system that performs processing in multiple locations. In some instances, computer system 300 may be interpreted as a single computing device, such as a distinct laptop, desktop computer, or the like, depending on the context.

Figure 4:
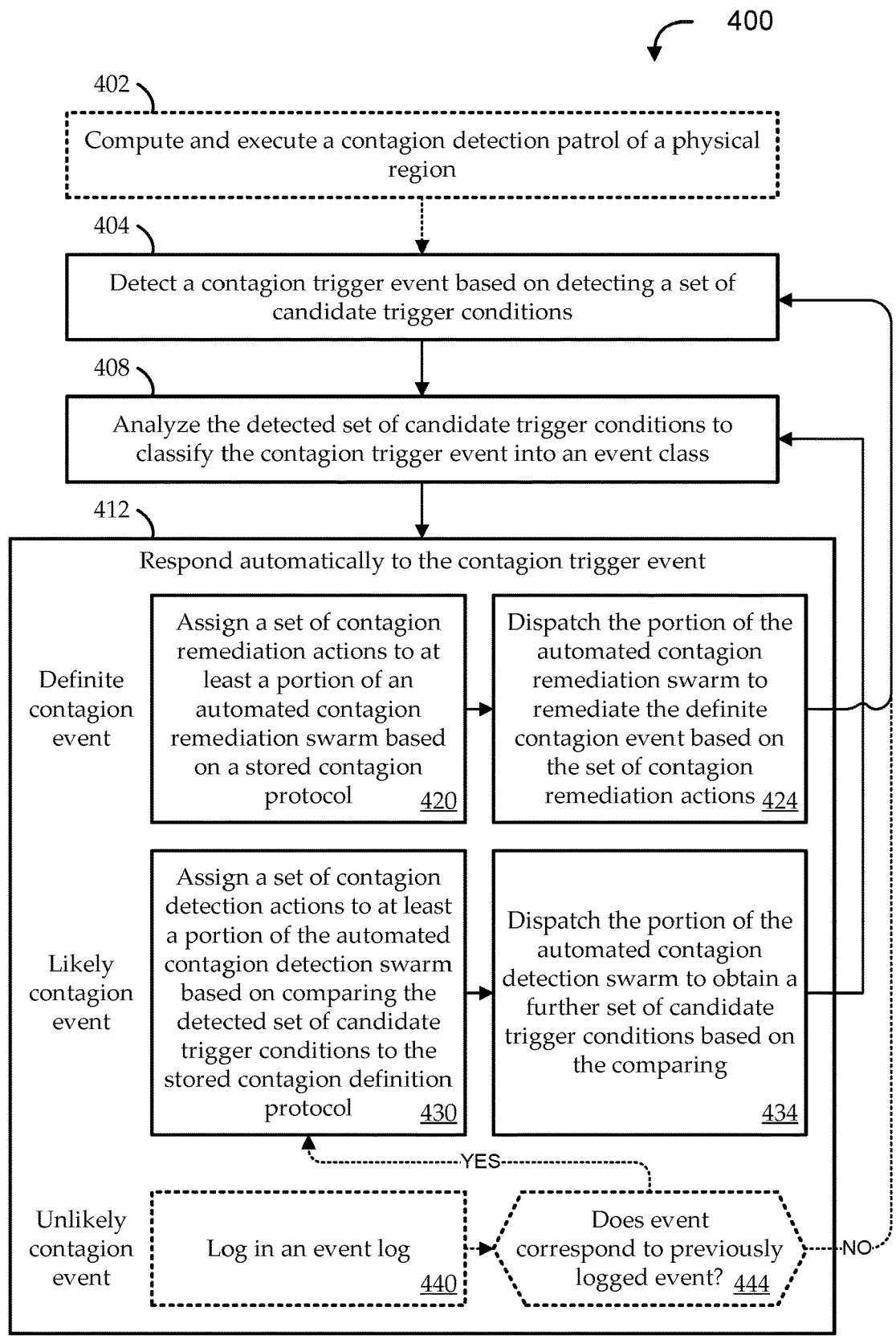
FIG. 4 shows a flow diagram of an illustrative method for automated detection and remediation of contagion events, according to various embodiments.

Systems including those described above can be used to implement various methods. FIG. 4 shows a flow diagram of an illustrative method 400 for automated detection and remediation of contagion events, according to various embodiments. Embodiments of the method 400 begin at stage 404 by detecting a contagion trigger event (e.g., by an automated contagion detection swarm in communication with a swarm controller) based on detecting a set of candidate trigger conditions. For example, the detecting at stage 404 can include using a sensor of a drone, configured as an automated mobile contagion sensor node of the automated contagion detection swarm, to obtain surface sample measurements and to determine that one or more of the surface sample measurements is indicative of one or more of the set of candidate trigger conditions. As another example, the detection at stage 404 can include using one or more cameras to obtain video data of a physical area, and monitoring the video data to detect a human interaction in the physical area indicative of one or more of the set of candidate trigger conditions. Some embodiments begin at stage 402 (prior to stage 404) by computing and executing a contagion detection patrol of a physical region (e.g., automatically by the swarm controller). For example, the automated contagion detection swarm is dispatched to obtain physical measurement data across a plurality of defined locations within the physical region to at least a predefined spatial resolution and measurement frequency (e.g., such that the measurements are close enough together in time and space).

Figure 5:
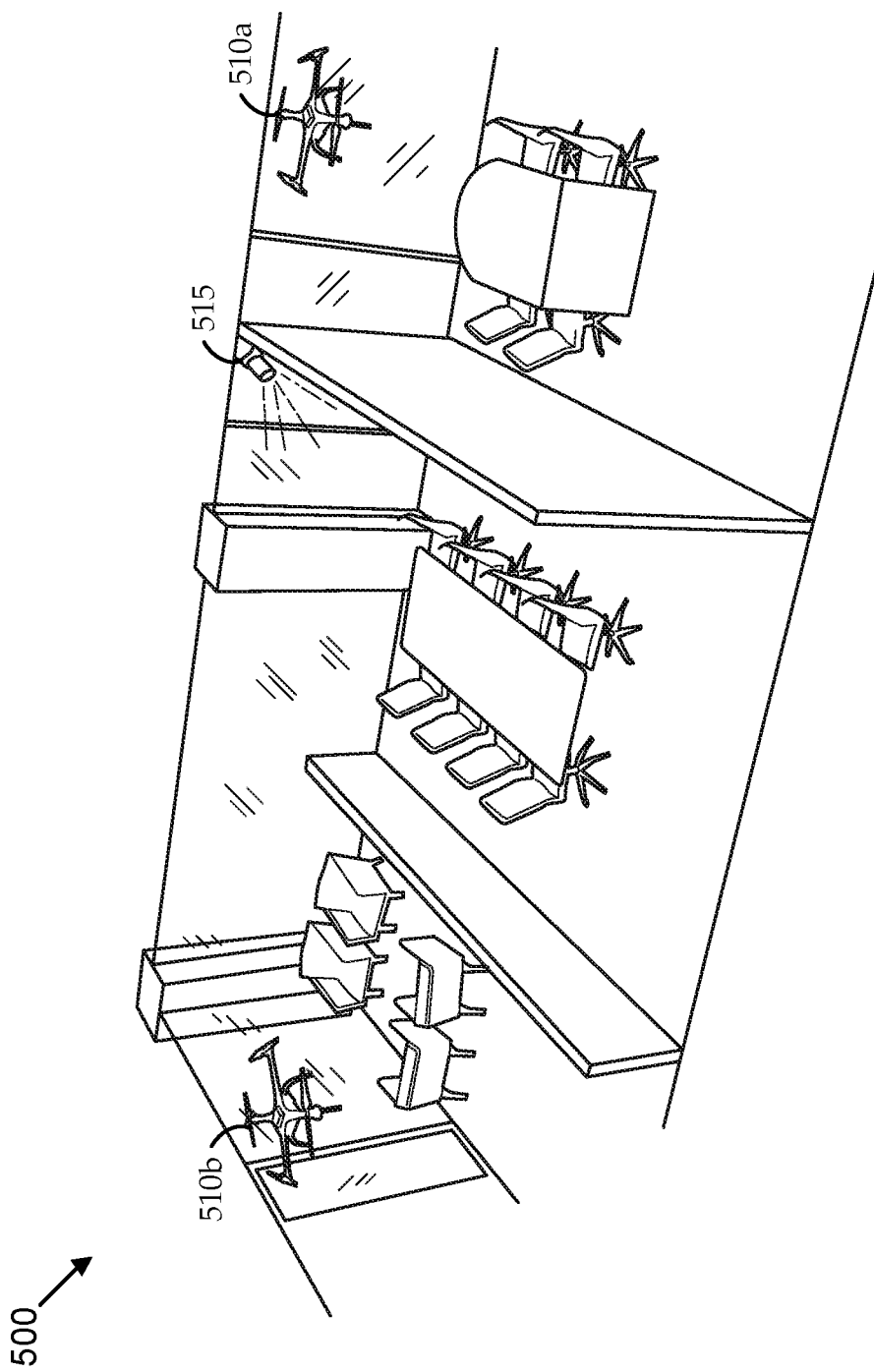
FIG. 5 shows automated contagion detection patrolling in an illustrative partial office environment.

For the sake of illustration, FIG. 5 shows an illustrative partial office environment 500 having a number of areas that can be populated by employees, visitors, and/or other individuals. For example, the right side of a full partition wall in the illustrated environment 500 shows a portion of an office with a small conference table and chairs; and the left side of the full partition wall in the illustrated environment 500 shows a larger area having a conference room with a larger conference table and chairs, and a separate break-out area with chairs. At least two drones 510 are patrolling the illustrated environment 500, and a security video camera 515 is mounted in a corner. Each of the two drones 510 can be configured as a mobile contagion sensor node of the automated contagion detection swarm to obtain surface sample measurements (e.g., and to determine that one or more of the surface sample measurements is indicative of one or more of the set of candidate trigger conditions). For example, over the course of a patrol, the drones 510 can use various types of sensors to obtain samples from any number of different non-human locations where contagions may be found, such as walls, windows, the half-wall partition, chairs, tables, floors, etc. Typically, such an environment can also include many other types of surfaces, such as plants and their containers, trash cans, bookcases and their contents, file cabinets, etc. The security video camera 515 can be configured as a fixed contagion sensor node of the automated contagion detection swarm. In some cases, concurrent with the patrol, and/or before or after the patrol, the security video camera 515 can obtain other sample measurements, such as air particulate measurements, temperature measurements, video footage, etc.

Returning to FIG. 4, at stage 408, embodiments can analyze the detected set of candidate trigger conditions (e.g., by the swarm controller) to classify the contagion trigger event into one of multiple event classes. The event classes can include a definite contagion event, a definite no-contagion event, and a likely contagion event. In some implementations, the event classes can also include an unlikely contagion event. As described herein, the classifying can involve comparing the detected sets of measurements to stored contagion profiles. Over time, the contagion profiles can be updated manually with updated contagion definitions and/or other parameters. In some embodiments, portions of the contagion profiles can be dynamically updated my machine learning algorithms, or the like.

At stage 412, embodiments can respond (e.g., automatically by the swarm controller) to the contagion trigger event in accordance with the classification at stage 408. For example, responsive to the analyzing at stage 408 resulting in classifying the contagion trigger event as the definite contagion event, the responding at stage 412 can include stages 420 and 424. At stage 420, embodiments can assign a set of contagion remediation actions to at least a portion of an automated contagion remediation swarm based on a stored contagion protocol. At stage 424, embodiments can dispatch the portion of the automated contagion remediation swarm to remediate the definite contagion event based on the set of contagion remediation actions. In some embodiments, responding at stage 412 to the analyzing at stage 408 resulting in classifying the contagion trigger event as the definite contagion event includes dispatching the portion of the automated contagion detection swarm to a physical region associated with the trigger event to obtain a plurality of physical measurement points, and defining an infected physical area for remediation based on the plurality of physical measurement points. In such embodiments, the dispatching the portion of the automated contagion remediation swarm to remediate at stage 424 can be based on the infected physical area for remediation. In some embodiments, responding at stage 412 to the analyzing at stage 408 resulting in classifying the contagion trigger event as the definite contagion event includes receiving an indication by the swarm controller from the portion of the automated contagion remediation swarm that the definite contagion event is remediated subsequent to the dispatching the portion of the automated contagion remediation swarm to remediate, and reclassifying the definite contagion event as a definite no contagion event responsive to the indication.

Figure 6:
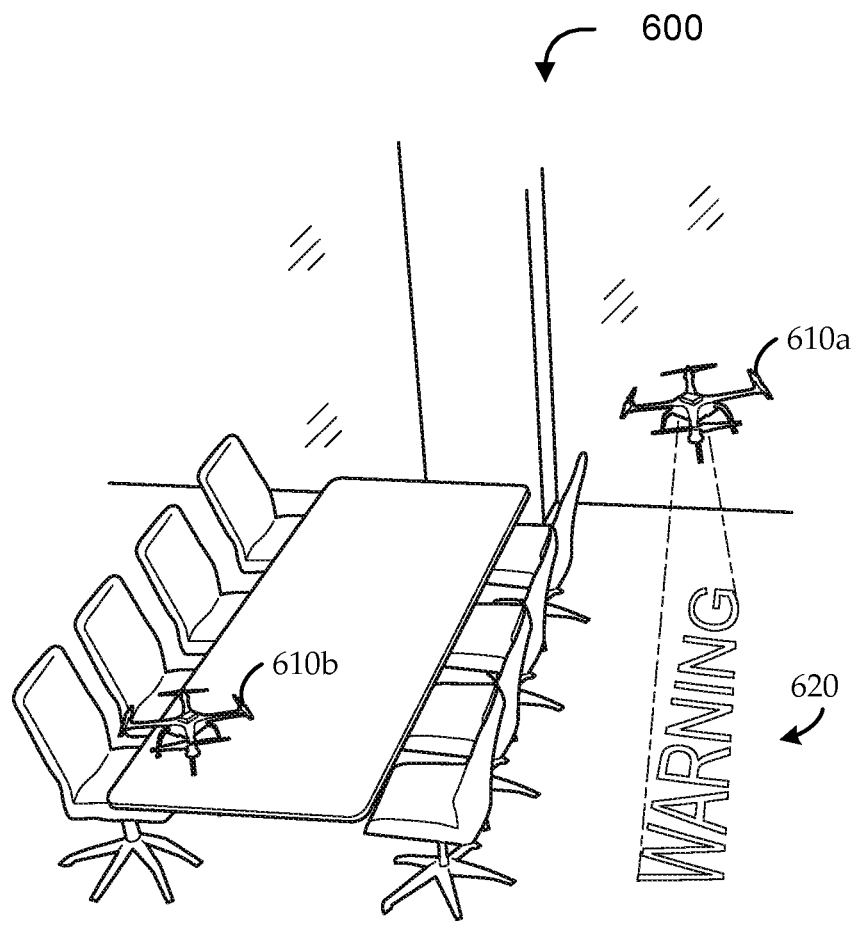
FIG. 6 shows automated contagion remediation in an illustrative conference room environment.

For the sake of illustration, FIG. 6 shows an illustrative conference room environment 600 having a conference table and chairs. It is assumed that analyzing at stage 408 of data obtained from the illustrated environment 600 resulted in classifying the contagion trigger event as a definite contagion event. As a result, at least two drones 610 have been dispatched for remediation. Each of the two drones 510 can be configured as a mobile contagion remediation node of the automated contagion remediation swarm to help remediate the definite contagion event in one or more ways. For example, contagion was specifically found on surfaces of the conference table. As illustrated, a first of the drones 610a is directed to hover in a region in front of the conference table relative to a direction from which individuals would likely approach the conference table. The drone 610a is projecting a conspicuous warning message 620 on the floor in front of the conference table to help ensure that individuals will not approach the table during remediation. Concurrently, a second drone 610b has landed on the conference table and is directly addressing the contagion event. For example, the second drone 610b may be applying disinfectant to the surface, wiping down the surface, shining ultraviolet light at the surface, etc.

Returning to FIG. 4, if the analyzing at stage 408 results in classifying the contagion trigger event as the likely contagion event, the responding at stage 412 can include stages 430 and 434. At stage 430, embodiments can assign a set of contagion detection actions to at least a portion of the automated contagion detection swarm based on comparing the detected set of candidate trigger conditions to the stored contagion definition protocol. At stage 434, embodiments can dispatch the portion of the automated contagion detection swarm to obtain a further set of candidate trigger conditions based on the comparing. As illustrated, some embodiments can then return to performing the analyzing at stage 408 and the responding at stage 412 (e.g., iteratively until a different event class results).

In some cases, the contagion trigger event detected in stage 404 is a present contagion trigger event, and the detected set of candidate trigger conditions is a present detected set of candidate trigger conditions. Responsive to the analyzing at stage 408 resulting in classifying the contagion trigger event as an unlikely contagion event, the responding at stage 412 can include stages 440 and 444. At stage 440, embodiments can log the unlikely contagion event in an event log. At stage 444, embodiments can determine whether a previous contagion trigger event was previously logged in the event log and corresponds to the present contagion trigger event based on correlating the present detected set of candidate trigger conditions with a previous detected set of candidate trigger conditions associated with the previous contagion trigger event. If it is determined at stage 444 that there is a correlating previously logged event, embodiments can return to stage 430 by reclassifying the present contagion trigger event as the likely contagion event. If it is determined at stage 444 that there is no correlating previously logged event, embodiments can return to stage 404 to wait for a further event detection.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. An automated contagion detection and remediation (ACDR) system comprising:
   a swarm controller to control operation of an automated contagion detection swarm and an automated contagion remediation swarm, the swarm controller comprising:
   a dispatcher subsystem to wirelessly schedule and direct the automated contagion detection swarm to execute a contagion detection patrol of a physical region;
   a classifier subsystem to analyze a detected set of candidate trigger conditions, obtained by one or more of plurality of mobile contagion sensor nodes in execution of the contagion detection patrol, to classify an associated contagion trigger event into one of a plurality of event classes, including a definite contagion event, a definite no-contagion event, and a likely contagion event;
   a remediater subsystem, coupled with the dispatcher subsystem and the classifier subsystem, to:
     respond to the classifier subsystem classifying the contagion trigger event as the definite contagion event by: assigning a set of contagion remediation actions to at least a portion of the automated contagion remediation swarm based on a stored contagion protocol; and directing the dispatcher subsystem further to dispatch the portion of the automated contagion remediation swarm to remediate the definite contagion event based on the set of contagion remediation actions; and
     respond to the classifier subsystem classifying the contagion trigger event as the likely contagion event by: assigning a set of contagion detection actions to at least a portion of the automated contagion detection swarm based on comparing the detected set of candidate trigger conditions to the stored contagion definition protocol; directing the dispatcher subsystem further to dispatch the portion of the automated contagion detection swarm to obtain a further set of candidate trigger conditions based on the comparing; and directing the classifier subsystem further to reclassify the trigger condition based on the further set of candidate trigger conditions.

2. The ACDR system of claim 1, further comprising:
   at least a first drone configured as a mobile contagion sensor node of the automated contagion detection swarm in wireless communication with, and at least partially under control of, the swarm controller; and
   at least a second drone configured as a mobile contagion remediation node of the automated contagion remediation swarm in wireless communication with, and at least partially under control of, the swarm controller.

3. The ACDR system of claim 1, further comprising:
   a drone, in wireless communication with and at least partially under control of the swarm controller, and configured both as a mobile contagion sensor node of the automated contagion detection swarm and as a mobile contagion remediation node of the automated contagion remediation swarm.

4. The ACDR system of claim 1, further comprising:
   a drone, in wireless communication with and at least partially under control of the swarm controller, and configured as a mobile contagion sensor node of the automated contagion detection swarm and/or as a mobile contagion remediation node of the automated contagion remediation swarm, the drone having an integrated autonomous physical access device by which to gain entry into one or more areas of the physical region via a closed doorway.

5. The ACDR system of claim 1, wherein the dispatcher subsystem is to execute the contagion detection patrol of a physical region, such that the automated contagion detection swarm obtains physical measurement data across a plurality of defined locations within the physical region to at least a predefined spatial resolution and measurement frequency.

6. The ACDR system of claim 1, wherein:
   the contagion trigger event is a present contagion trigger event, and the detected set of candidate trigger conditions is a present detected set of candidate trigger conditions;
   the plurality of event classes further includes an unlikely contagion event; and
   the remediater subsystem is further to respond to the classifier subsystem classifying the contagion trigger event as the unlikely contagion event by:
     logging the unlikely contagion event in an event log;
     determining whether a previous contagion trigger event was previously logged in the event log and corresponds to the present contagion trigger event based on correlating the present detected set of candidate trigger conditions with a previous detected set of candidate trigger conditions associated with the previous contagion trigger event; and
     responsive to determining that the previous contagion trigger event corresponds to the present contagion trigger event based on the correlating, directing the classifier subsystem to reclassify the present contagion trigger event as the likely contagion event, and performing the responding to the classifier subsystem classifying the contagion trigger event as the likely contagion event.

7. The ACDR system of claim 1, further comprising:
   at least one automated mobile contagion sensor node of the automated contagion detection swarm, and at least one static contagion sensor node of the automated contagion detection swarm.

8. The ACDR system of claim 7, wherein:
   the at least one static contagion sensor node of the automated contagion detection swarm comprises a video camera mounted in a fixed position in the physical region.

9. The ACDR system of claim 1, further comprising:
   a memory having the stored contagion definition protocol stored thereon, the stored contagion definition protocol defining a plurality of candidate trigger conditions comprising the detected set of candidate trigger conditions and the further set of candidate trigger conditions.

10. The ACDR system of claim 1, wherein the remediater subsystem is to respond to the classifier subsystem classifying the contagion trigger event as the definite contagion event further by:
    dispatching the portion of the automated contagion detection swarm to a location associated with the detected set of candidate trigger conditions to obtain a plurality of physical measurement points; and
    defining an infected physical area for remediation based on the plurality of physical measurement points, wherein the directing the dispatcher subsystem to dispatch the portion of the automated contagion remediation swarm to remediate is based on the infected physical area for remediation.

11. The ACDR system of claim 1, wherein the remediater subsystem is to respond to the classifier subsystem classifying the contagion trigger event as the definite contagion event further by:
receiving an indication by the swarm controller from the portion of the automated contagion remediation swarm that the definite contagion event is remediated subsequent to the dispatching the portion of the automated contagion remediation swarm to remediate; and
reclassifying the definite contagion event as a definite no contagion event responsive to the indication.

12. The ACDR system of claim 1, wherein the remediater subsystem is to respond to the classifier subsystem classifying the contagion trigger event as the definite contagion event further by directing the dispatcher subsystem further to dispatch the portion of the automated contagion remediation swarm to remediate by assigning at least one drone, as an automated mobile contagion remediation node of the automated contagion remediation swarm, to execute a disinfecting routine in an infected physical area associated with the trigger event.

13. The ACDR system of claim 1, wherein the remediater subsystem is to respond to the classifier subsystem classifying the contagion trigger event as the definite contagion event further by directing the dispatcher subsystem further to dispatch the portion of the automated contagion remediation swarm to remediate by assigning at least one drone, as an automated mobile contagion remediation node of the automated contagion remediation swarm, to execute a cordoning routine around an infected physical area associated with the trigger event.

14. A method comprising:
detecting a contagion trigger event, by an automated contagion detection swarm in communication with a swarm controller, based on detecting a set of candidate trigger conditions;
analyzing the detected set of candidate trigger conditions, by the swarm controller, to classify the contagion trigger event into one of a plurality of event classes, including a definite contagion event, a definite no-contagion event, and a likely contagion event; and
responding, automatically by the swarm controller, to the contagion trigger event by:
responsive to the analyzing resulting in classifying the contagion trigger event as the definite contagion event: assigning a set of contagion remediation actions to at least a portion of an automated contagion remediation swarm based on a stored contagion protocol; and dispatching the portion of the automated contagion remediation swarm to remediate the definite contagion event based on the set of contagion remediation actions; and
responsive to the analyzing resulting in classifying the contagion trigger event as the likely contagion event: assigning a set of contagion detection actions to at least a portion of the automated contagion detection swarm based on comparing the detected set of candidate trigger conditions to the stored contagion definition protocol, dispatching the portion of the automated contagion detection swarm to obtain a further set of candidate trigger conditions based on the comparing; and returning to performing the analyzing and the responding.

15. The method of claim 14, further comprising:
computing and executing a contagion detection patrol of a physical region, automatically by the swarm controller, by dispatching the automated contagion detection swarm, such that the automated contagion detection swarm obtains physical measurement data across a plurality of defined locations within the physical region to at least a predefined spatial resolution and measurement frequency.

16. The method of claim 14, wherein:
the contagion trigger event is a present contagion trigger event, and the detected set of candidate trigger conditions is a present detected set of candidate trigger conditions;
the plurality of event classes further includes an unlikely contagion event;
responsive to the analyzing resulting in classifying the present contagion trigger event as the unlikely contagion event:
logging the unlikely contagion event in an event log;
determining whether a previous contagion trigger event was previously logged in the event log and corresponds to the present contagion trigger event based on correlating the present detected set of candidate trigger conditions with a previous detected set of candidate trigger conditions associated with the previous contagion trigger event; and
responsive to determining that the previous contagion trigger event corresponds to the present contagion trigger event based on the correlating, reclassifying the present contagion trigger event as the likely contagion event, and returning to performing the analyzing and the responding.

17. The method of claim 14, wherein the detecting the contagion trigger event comprises using a sensor of a drone, configured as an automated mobile contagion sensor node of the automated contagion detection swarm, to obtain a plurality of surface sample measurements and to determine that one or more of the surface sample measurements is indicative of one or more of the set of candidate trigger conditions.

18. The method of claim 14, wherein the detecting the contagion trigger event comprises using one or more cameras to obtain video data of a physical area, and monitoring the video data to detect a human interaction in the physical area indicative of one or more of the set of candidate trigger conditions.

19. The method of claim 14, further comprising, responsive to the analyzing resulting in classifying the trigger event as the definite contagion event:
dispatching the portion of the automated contagion detection swarm to a physical region associated with the trigger event to obtain a plurality of physical measurement points; and
defining an infected physical area for remediation based on the plurality of physical measurement points,
wherein the dispatching the portion of the automated contagion remediation swarm to remediate is based on the infected physical area for remediation.

20. The method of claim 14, further comprising, responsive to the analyzing resulting in classifying the trigger event as the definite contagion event:

receiving an indication by the swarm controller from the portion of the automated contagion remediation swarm that the definite contagion event is remediated subsequent to the dispatching the portion of the automated contagion remediation swarm to remediate; and
reclassifying the definite contagion event as a definite no contagion event responsive to the indication.

\* \* \* \* \*